United States Patent
Lindberg et al.

(10) Patent No.: US 7,113,829 B2
(45) Date of Patent: Sep. 26, 2006

(54) IMPLANTABLE MEDICAL DEVICE SYSTEM WITH MINIMIZATION OF ENERGY EMPLOYED FOR PROCESSING DATA

(75) Inventors: Magnus Lindberg, Sundbyberg (SE); Mats Arturson, Taby (SE)

(73) Assignee: St. Jude Medical AB, Jarfalla (SE)

( * ) Notice: Subject to any disclaimer, the term of this patent is extended or adjusted under 35 U.S.C. 154(b) by 557 days.

(21) Appl. No.: 10/307,829

(22) Filed: Dec. 2, 2002

(65) Prior Publication Data

US 2003/0163173 A1 Aug. 28, 2003

(30) Foreign Application Priority Data

Feb. 28, 2002 (SE) .................................. 0200625

(51) Int. Cl.
*A61N 1/08* (2006.01)
(52) U.S. Cl. .......................................... 607/60; 607/32
(58) Field of Classification Search ........ 128/897–898, 128/920; 600/300, 522–523; 607/1–2, 29–32, 607/59–60
See application file for complete search history.

(56) References Cited

U.S. PATENT DOCUMENTS

| | | | |
|---|---|---|---|
| 5,464,435 A * | 11/1995 | Neumann | 607/9 |
| 5,603,331 A | 2/1997 | Heemels et al. | |
| 5,697,959 A * | 12/1997 | Poore | 607/32 |
| 5,819,740 A | 10/1998 | Muhlenberg | |
| 5,876,425 A | 3/1999 | Gord et al. | |
| 6,161,043 A | 12/2000 | McClure et al. | |
| 6,190,324 B1 * | 2/2001 | Kieval et al. | 600/483 |
| 6,409,675 B1 * | 6/2002 | Turcott | 600/508 |
| 6,658,283 B1 * | 12/2003 | Bornzin et al. | 600/510 |
| 2001/0051766 A1 * | 12/2001 | Gazdzinski | 600/309 |
| 2002/0151812 A1 * | 10/2002 | Scheiner et al. | 600/528 |

FOREIGN PATENT DOCUMENTS

WO WO 01/17609 3/2001

* cited by examiner

*Primary Examiner*—Robert E. Pezzuto
*Assistant Examiner*—Kristen Mullen
(74) *Attorney, Agent, or Firm*—Schiff Hardin LLP

(57) ABSTRACT

In a method for operating a system having an implantable medical device that communicates by wireless telemetry data exchange with an external unit, an algorithm is employed, selecting either an internal calculation processor in the implantable device or an external calculation processor in the external unit for accomplishing a given data processing. If the sum of an estimated amount of energy to process the data in the internal calculation processor and an estimated amount of energy required to then transmit an expected amount of result data to the external unit exceeds an estimated amount of energy required to transmit the source data to the external unit, the external calculation processor is selected. Otherwise, the internal calculation processor is selected. The method thereby results in a minimal energy consumption in the implantable medical device. This, in turn, allows for a device with a long battery lifetime and thus an improved patient comfort.

15 Claims, 2 Drawing Sheets

IMPLANTABLE MEDICAL DEVICE SYSTEM WITH MINIMIZATION OF ENERGY EMPLOYED FOR PROCESSING DATA

BACKGROUND OF THE INVENTION

1. Field of the Invention

The present invention relates generally to an implantable medical device that is associated with telemetry means for wireless data exchange with external unit of the type wherein each of the implantable device each has a calculation processor.

2. Description of the Prior Art

Conventionally the data processing capacity in implantable medical devices has been relatively restricted, primarily due to limitations in the internal memory and processing capacity. However, the amount of processing in the devices has also been kept low in order to economize the energy resources therein. Therefore, raw data generally have been transferred from the implantable device to an external unit for processing whenever a more extensive data analysis has been requested.

U.S. Pat. No. 5,603,331 discloses a data logging system for an implantable cardiac device with a capability of computing and storing histogram arrays of heart rate variability data over a prolonged period of time. A logarithmic data compression algorithm is used to save memory and energy resources in the cardiac device.

U.S. Pat. No. 6,161,043 describes another example of an implantable cardiac device having event recording capability with data compression. A compressed electrogram signal is transmitted from the implantable device to an external programmer according to the following. First, an uncompressed starting value is sent. Nevertheless, following signal samples are sent in the form of delta signals in respect of the starting value. Finally, based on the delta signal, the programmer produces a decompressed signal, which may be presented graphically.

In recent years, however, the processing and data storage capacity of implantable medical devices has increased dramatically. Additionally, battery technology has made many important advancements. Although the external data processing saves energy in the implantable medical device, the process of transferring the source data from the device to the external processing unit also consumes energy. In view of today's comparatively competent processors it is therefore no longer self-evident that external processing is always preferable to internal processing. In fact, transferring the raw data from the implantable medical device may very well demand more energy than performing the calculation in the device and instead transmit the result data for external presentation or further processing.

SUMMARY OF THE INVENTION

It is an object of the present invention to address this problem and thus provide an improved solution in an implantable medical device system.

According to the invention this object is achieved by a method in an implantable medical device system as described initially, wherein the location for performing a processing between a first calculation processor in the implantable device and the second calculation processor in the external device, based on a selection algorithm.

An important advantage attained by this strategy is that the location for any relatively demanding data processing operation may be selected such that a minimal amount of energy resources is used in the implantable medical device. This, in turn, allows for a device with a long battery lifetime and thus improved patient comfort.

According to a preferred embodiment of the inventive method, the selection algorithm involves consideration of a first estimated energy amount for performing the processing in the first calculation processor plus transmitting an expected amount of result data over a channel between the first wireless interface and the second wireless interface. The algorithm also involves consideration of a second estimated energy amount for instead transmitting the source data over the channel. Finally, a comparison is made between the first estimated energy amount and the second estimated energy amount. The smallest amount of energy then determines the location for performing the processing, such that the location is selected which results in the lowest energy consumption in the implantable medical device.

According to another preferred embodiment of the inventive method, the selection algorithm takes into account an estimated required amount of processing to generate the result data. An advantage attained by considering this parameter is that a threshold may be set, such that all processing tasks below a certain complexity (or amount) is always processed by a predefined processor. Thus, these operations will not be subject to any evaluation as to the location of the processing. This, in turn, saves energy in the implantable medical device. In any case, an estimation of the expected amount of processing to be performed provides an important basis for the decision algorithm.

According to yet another preferred embodiment of the inventive method, the selection algorithm takes into account a current capacity of a channel between the first wireless interface and the second wireless interface. It is advantageous to consider this parameter, since due to variations in the radio environment, the channel's quality may vary from excellent to extremely poor. In the former case, transmitting the source data for external processing may be preferable (i.e. in the second calculation processor), whereas in the latter case, internal processing (i.e. in the first calculation processor) will typically be preferable. A low quality channel is namely inclined to require a comparatively large number of re-transmissions and consequently be both time and energy consuming.

In another preferred embodiment of the inventive method, the selection algorithm takes into account an amount of overhead data required to transmit the source data and/or an estimated amount of result data over a channel between the first wireless interface and the second wireless interface. It is desirable to consider the overhead data when selecting the location for performing a certain data processing, since it is the total amount of data, which must be transmitted that determines the most advantageous location. Moreover, due to the nature of the data (i.e. whether is represents source data or result data), different overhead data may be demanded. Furthermore, the amount of overhead data may be due to the channel quality.

The above object also is achieved in accordance with the invention by a computer program directly loadable into the internal memory of a digital computer, having software for executing the inventive method described above when said program is run on a computer.

The above object also is achieved in accordance with the invention by a computer readable medium, having a program recorded thereon, where the program causes a computer perform the method described above.

The above object also is achieved in accordance with the invention by an implantable medical device system as described initially, wherein at least one of the implantable medical device and the external unit includes a selector, which selects the location for performing a processing between the first calculation processor and the second calculation processor. The selector operates according to a selection algorithm. This design is advantageous, since it allows selection of the location for a data processing operation, such that a minimal amount of energy resources is used in the implantable medical device. This, in turn, allows for a device with a long battery lifetime and thus an improved patient comfort.

According to a preferred embodiment of the inventive system, the external unit contains a programmer unit, which is adapted to read information from the implantable medical device and update the contents of one or more digital storages therein. A typical situation when resource demanding data processing may be required is when a physician examines whether a particular device has parameter settings, which are optimal with respect to the patient into which the device is implanted. In these situations, the physician utilizes a programmer. Therefore, it is advantageous to combine the programmer function with the proposed external processing option.

According to another preferred embodiment of the inventive system, the external unit instead includes a repeater station, which is adapted to communicate with a particular implantable medical device and at least one remote surveillance and/or programming unit. Irrespective of whether the repeater station is mobile or stationary, it may take over any more demanding data processing tasks that are placed on the implantable medical device whenever this device is located within a communication range of the repeater station. Again, this increases the chances of obtaining a device with a prolonged battery lifetime.

Although the proposed solution is primarily intended for cardiac devices, such as pacemakers and defibrillators, the invention is equally applicable to any alternative type of implantable medical device, for example drug pumps or neurostimulators.

DESCRIPTION OF THE PREFERRED EMBODIMENTS

Figure 1:
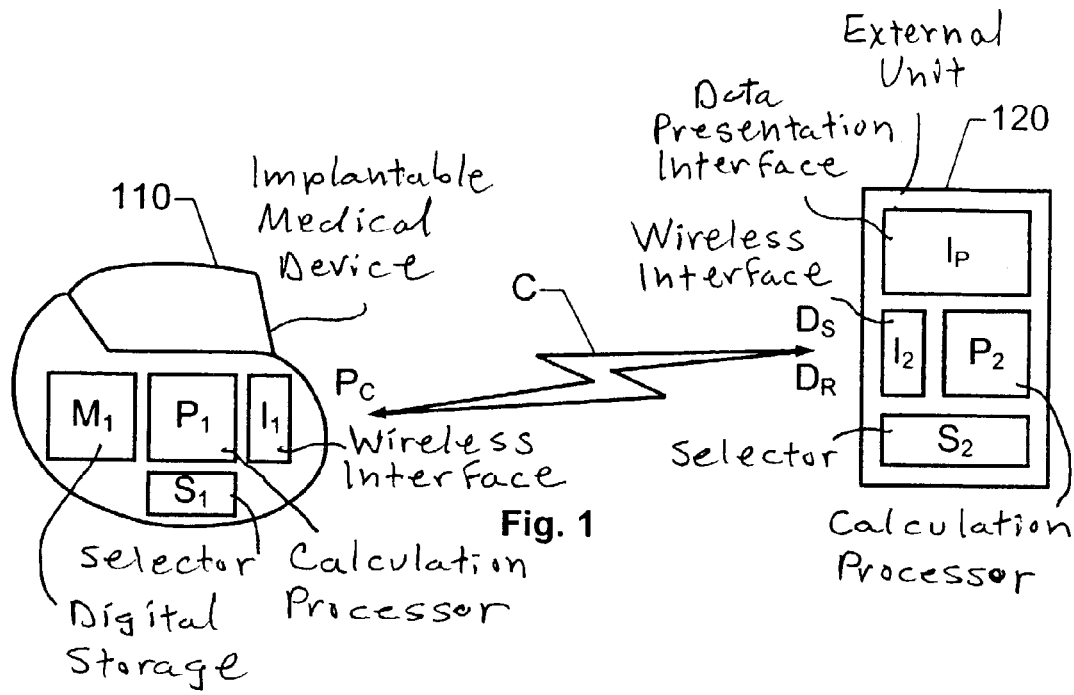
FIG. 1 schematically illustrates an implantable medical device system according to an embodiment of the invention.

FIG. 1 shows an implantable medical device system according to an embodiment of the invention. The system includes an implantable medical device 110 and an external unit 120, which may communicate with each other via a channel C. For example, the implantable medical device 110 receives program code PC from the external unit 120 and transmits various kinds of measurement data DS, DR in the opposite direction.

In addition to, for instance a cardiac pacing compounds, the implantable medical device 110 contains a first wireless interface $I_1$, a first calculation processor $P_1$, a first selector $S_1$ and a digital storage $M_1$. The external unit 120 contains a second wireless interface $I_2$, a second calculation processor $P_2$, a second selector $S_2$ and a data presentation interface $I_P$.

The channel C is set up between the first wireless interface $I_1$ and the second wireless interface $I_2$, for example as a bi-directional radio link. Thereby, the digital storage $M_1$ may be updated with program code Pc and/or parameter settings pertaining to the mode of operation of the device 110 may be received. According to preferred embodiment of the invention, the external unit 120 namely includes a programmer unit or a repeater station.

When the channel C has been established and the device 110 comes across a data processing task of at least a certain complexity (or amount), a decision is made as to whether the processing shall be carried out either by the first calculation processor $P_1$ (in the device 110) or the second calculation processor $P_2$ (in the external unit 120). This decision may be made by the first selector $S_1$ or by the second selector $S_2$. According to a preferred embodiment of the invention, however, the second selector $S_2$ in the external unit 120 effects the decision in order to save energy in the implantable medical device 110. Nevertheless, in most cases the device 110 will trigger the decision process.

Regardless of whether the decision is that the processing should be performed by the first calculation processor $P_1$ and therefore result data $D_R$ will be transmitted to the external unit 120 after completed processing, or the decision is that the processing should be performed by the second calculation processor $P_2$ and consequently unprocessed source data $D_S$ will be transmitted to the external unit 120 instead, the result data $D_R$ (or a parameter derived there from) preferably are presented in a user-friendly format via the data presentation interface $I_P$. In any case, the selectors $S_1$ and $S_2$ operate according to a selection algorithm, which will be described below with reference to FIGS. 2 and 3.

Figure 2:
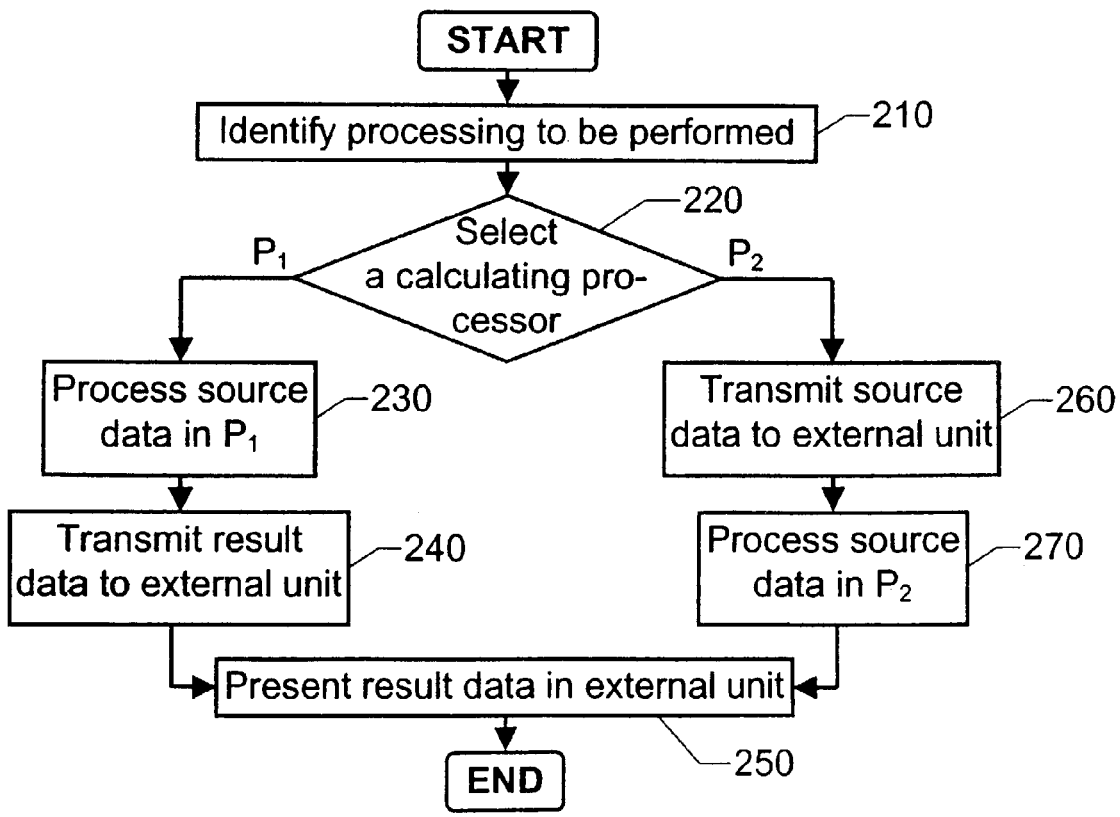
FIG. 2 is a flow diagram showing the general operating principle according to the invention.

FIG. 2 illustrates, by means of a flow diagram, the general operating principle according of the invention. A first step 210, identifies a processing to be performed, which is subject to a decision as to a selection between an internal or an external processor. Typically, a choice of calculating processor only arises if a channel C has already been established between the implantable medical device in question and at least one external unit. Moreover, the amount or complexity of the data processing should preferably exceed a predetermined threshold value. A following step 220 investigates, based on a selection algorithm, whether an internal processor P1 or an external processor P2 should be used. In the former case, a step 230 processes the source data into corresponding result data after which a step 240 transmits the result data via the channel C to the external unit. Otherwise, a step 260 transmits the source data to the external unit via the channel C. Subsequently, a step 270 processes the source data into corresponding result data. After the steps 240 and 270 respectively, a step 250 presents the result data in the external unit, preferably on a graphical format and by means of a data presentation interface adapted therefor.

According to a preferred embodiment of the invention, the selection algorithm on which the selection in the step 220 is based, takes into account one or more of the following parameters: an estimated amount of processing required to generate the result data, a current capacity of the channel between the implantable medical device and the external unit (i.e. between the first wireless interface $I_1$ and the second wireless interface $I_2$ in FIG. 1) and an amount of overhead data required to transmit the source data and/or the result data over this channel. The selection algorithm seeks, for a given (estimated) amount of result data, to minimize the energy consumption in the implantable medical device per data bit in the result data.

In general, an acceptably low bit error rate (BER) for the data transmission is desired. This may be accomplished by a variation of the output power, the channel bandwidth and/or the degree of forward error correction (FEC) coding. In most cases, the bandwidth is determined by a standardized protocol according to which the wireless interfaces $I_1$ and $I_2$ operate and/or the type of modulation which these interfaces can handle. Likewise, the possibilities to vary the FEC-coding are normally rather restricted. Consequently, varying the output power, as a rule, will be the most important means to obtain an acceptable BER.

Figure 3:
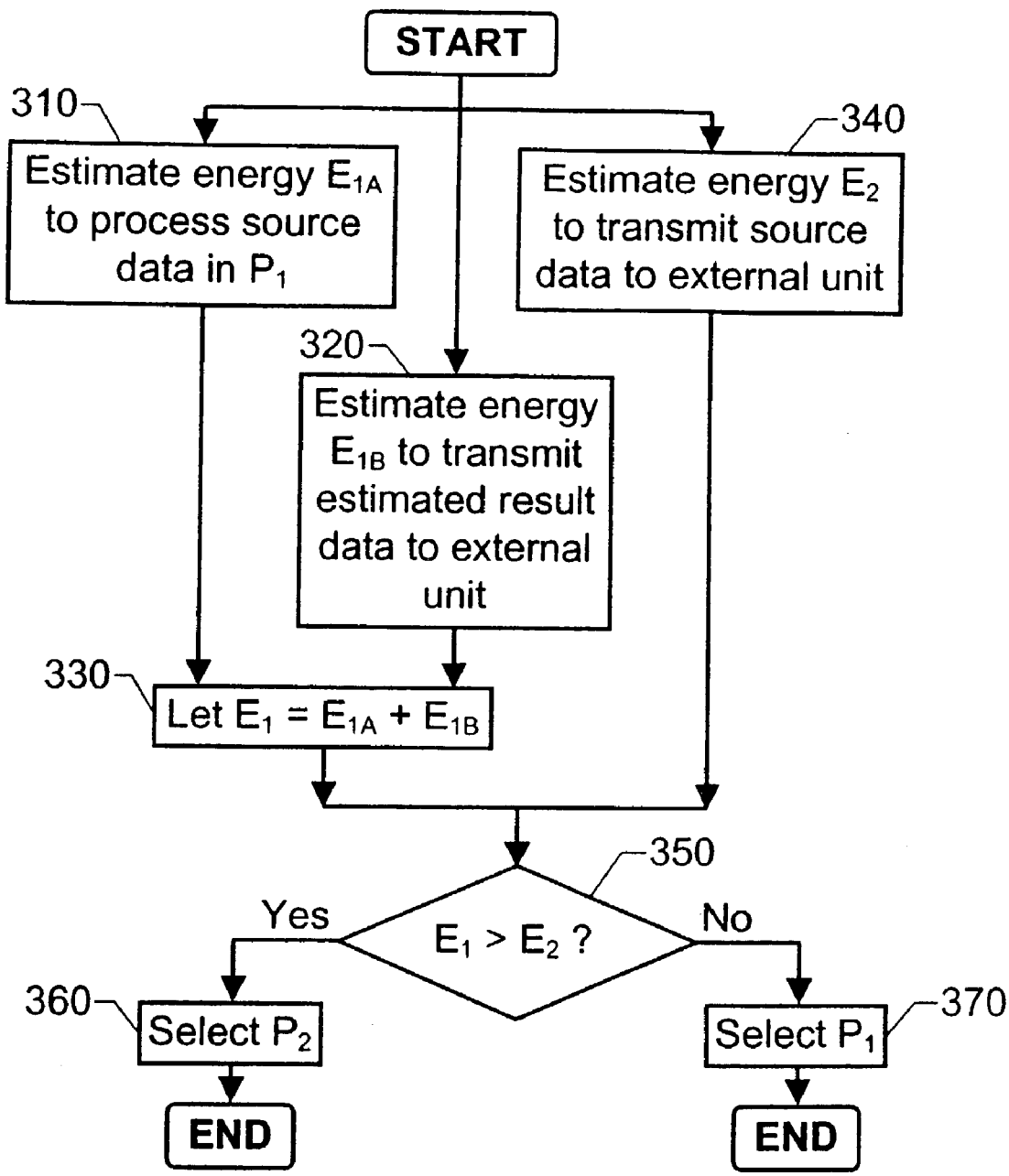
FIG. 3 is a flow diagram showing a method of selecting a calculation processor for a data processing task according to an embodiment of the invention.

As a summary, the general method for selecting a calculation processor for a data processing task according to an embodiment of the invention will be described with reference to FIG. 3.

A first step 310 estimates a first amount of energy E1A required to process a given set of source data into corresponding result data in the first calculation processor $P_1$ (i.e. in the implantable medical device). Another step 320, estimates a second amount of energy $E_{1B}$ required to transmit an expected amount of result data to the external unit. As mentioned earlier, this estimation may take into consideration a current capacity and quality of the channel between the implantable medical device and the external unit and the amount of overhead data required. Another step 340 estimates a second decision energy $E_2$ required to transmit the given set of source data to the external unit. Preferably, but not necessarily, two or more of the steps 310, 320 and 340 are executed in parallel.

A step 330 adds the first amount of energy $E_{1A}$ to the second amount of energy $E_{1B}$ to obtain a first decision energy $E_1$. After that, a step 350 compares the first decision energy $E_1$ with the second decision energy $E_2$, and depending on which is larger, a step 360 or a step 370 selects external processing (i.e. in $P_2$) or internal processing (i.e. in $P_1$) respectively. If the first decision energy $E_1$ is larger than the second decision energy $E_2$, external processing is selected. Otherwise, internal processing is selected.

All of the process steps, as well as any sub-sequence of steps, described with reference to the FIG. 3 above may be controlled by means of a computer program being directly loadable into the internal memory of a computer, which includes appropriate software for controlling the necessary steps when the program is run on a computer. Furthermore, such computer program can be recorded onto arbitrary kind of computer readable medium as well as be transmitted over arbitrary type of network and transmission medium.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating an implantable medical device system having an implantable medical device which includes a first calculation processor and an external unit, in wireless communication with said implantable medical device, including a second calculation processor, said method comprising the steps of:
    identifying a processing task involving processing of source data into result data;
    executing a selection algorithm in one of said first calculation processor and said second calculation processor to select one of said first calculation processor and said second calculation processor, as a selected processor, to perform said processing task; and
    performing said processing task in said selected processor and presenting said result data at said external unit.

2. A method as claimed in claim 1 wherein the step of executing said selection algorithm includes the steps of:
    estimating a first estimated energy amount for performing said processing task in said first calculation processor, estimating a size of the result data resulting from said processing task, and including, in said first estimated energy amount, energy for transmitting said result data of said estimated size wirelessly from said implantable medical device to said external unit;
    estimating a second energy amount for transmitting source data needed for said processing task wirelessly from said implantable medical device to said external unit; and
    comparing said first estimated energy amount and said second estimated energy amount and selecting said first calculation processor to perform said processing task if said first estimated energy amount is less than said second estimated energy amount and selecting said second calculation processor for performing said processing task if said second estimated energy amount is less than said first estimated energy amount.

3. A method as claimed in claim 2 wherein the step of estimating said first energy amount includes estimating an amount of processing required to generate said result data in said first calculation processor.

4. A method as claimed in claim 1 wherein said implantable medical device and said external unit wirelessly communicate via a channel between a first wireless interface in said implantable medical device and a second wireless interface in said external unit, and wherein the step of estimating said first estimated energy amount takes a current capacity of said channel into account and wherein the step of estimating said second estimated energy amount also takes said current capacity of said channel into account.

5. A method as claimed in claim 1 wherein said implantable medical device and said external unit wirelessly communicate via a channel between a first wireless interface disposed in said implantable medical device and a second wireless interface disposed in said external unit, and wherein the step of executing said selection algorithm includes taking into account an amount of overhead data required to transmit at least one of said source data and said result data via said channel from said first wireless interface to said second wireless interface.

6. A computer readable medium having a computer program stored therein for operating an implantable medical device system having an implantable medical device which includes a first calculation processor and an external unit, in wireless communication with said implantable medical device, including a second calculation processor, said computer readable medium being loadable into one of said first and second calculation processors and thereby programming said one of said first and second calculation processors to:
    identify a processing task involving processing of source data into result data for subsequent presentation at said external unit;
    execute a selection algorithm in said computer to select one of said first calculation processor and said second calculation processor to perform said processing task.

7. A computer readable medium as claimed in claim 6 wherein said computer program programs said one of said first and second calculation processors to execute algorithm by:
    estimating a first estimated energy amount for performing said processing task in said first calculation processor, estimating a size of the result data resulting from said processing task, and including, in said first estimated energy amount, energy for transmitting said result data of said estimated size wirelessly from said implantable medical device to said external unit;

estimating a second energy amount for transmitting source data needed for said processing task wirelessly from said implantable medical device to said external unit; and comparing said first estimated energy amount and said second estimated energy amount and selecting said first calculation processor to perform said processing task if said first estimated energy amount is less than said second estimated energy amount and selecting said second calculation processor for performing said processing task if said second estimated energy amount is less than said first estimated energy amount.

8. A computer readable medium as claimed in claim 7 wherein said computer program programs said one of said first and second calculation processors to estimate said first energy amount by estimating an amount of processing required to generate said result data in said first calculation processor.

9. A computer readable medium as claimed in claim 6 wherein said implantable medical device and said external unit wireless communicate via a channel between a first wireless interface in said implantable medical device and a second wireless interface in said external unit, and wherein said said computer program programs said one of said first and second calculation processors to estimate said first estimate energy amount by taking a current capacity of said channel into account and estimates said second estimated energy amount also by taking said current capacity of said channel into account.

10. A computer readable medium as claimed in claim 6 wherein said implantable medical device and said external unit wirelessly communicate via a channel between a first wireless interface disposed in said implantable medical device and a second wireless interface disposed in said external unit, and wherein said computer program programs said one of said first and second calculation processors to estimate selection algorithm by taking into account an amount of overhead data required to transmit at least one of said source data and said result data via said channel from said first wireless interface to said second wireless interface.

11. A medical device system comprising:

an implantable medical device which includes a first calculation processor;

an external unit, in wireless communication with said implantable medical device, including a second calculation processor;

after identifying a processing task involving processing of source data into result data, one of said first calculation processor and said second calculation processor executing a selection algorithm to select one of said first calculation processor and said second calculation processor, as a selected processor, to perform said processing task; and said selected processor performing said processing task and presenting said result data at said external unit.

12. A medical device system as claimed in claim 11 wherein said one of said first and second calculation processors that executes said selection algorithm:

estimates a first estimated energy amount for performing said processing task in said first calculation processor, estimates a size of the result data resulting from said processing task, and includes, in said first estimated energy amount, an estimated energy for transmitting said result data of said estimated size wirelessly from said implantable medical device to said external unit;

estimates a second energy amount for transmitting source data needed for said processing task wirelessly from said implantable medical device to said external unit; and compares said first estimated energy amount and said second estimated energy amount and selects said first calculation processor to perform said processing task if said first estimated energy amount is less than said second estimated energy amount and selects said second calculation processor for performing said processing task if said second estimated energy amount is less than said first estimated energy amount.

13. A medical device system as claimed in claim 12 wherein said one of said first and second calculation processors that executes said selection algorithm estimates said first energy amount by estimating an amount of processing required to generate said result data in said first calculation processor.

14. A medical device system as claimed in claim 11 wherein said implantable medical device contains a first wireless interface and wherein said external unit contains second wireless interface, and wherein said implantable medical device and said external unit wirelessly communicate via a channel between said first wireless interface and said second wireless interface, and wherein said one of said first and second calculation processors that executes said selection algorithm estimates said first estimated energy amount by taking a current capacity of said channel into account and estimates said second estimated energy amount also by taking said current capacity of said channel into account.

15. A medical device system as claimed in claim 11 wherein said implantable medical device contains a first wireless interface and wherein said external unit contains second wireless interface, and wherein said implantable medical device and said external unit wirelessly communicate via a channel between said first wireless interface and said second wireless interface, and wherein said one of said first and second calculation processors that executes said selection algorithm takes into account an amount of overhead data required to transmit at least one of said source data and said result data via said channel from said first wireless interface to said second wireless interface.

* * * * *